United States Patent [19]

Kurono et al.

[11] Patent Number: 5,177,102

[45] Date of Patent: Jan. 5, 1993

[54] POLYISOPRENE COMPOUNDS AND SALTS THEREOF

[75] Inventors: Masayasu Kurono; Yasuaki Kondo; Takuji Yamaguchi; Ryoichi Unno; Hiromoto Kimura; Noboru Kuboyama; Takashi Ito; Mitsuru Oka; Akira Tashita; Kazumasa Nakano; Kiichi Sawai, all of Nagoya, Japan

[73] Assignee: Sanwa Kagaku Kenkyusho Co., Ltd., Nagoya, Japan

[21] Appl. No.: 695,121

[22] Filed: May 3, 1991

[30] Foreign Application Priority Data

May 9, 1990 [JP] Japan ................. 2-117702

[51] Int. Cl.$^5$ ............... A61K 31/40; C07D 209/52
[52] U.S. Cl. .................. 514/413; 514/418;
514/421; 548/453; 564/501; 564/509; 564/511;
564/512
[58] Field of Search ............... 548/512, 452, 453;
564/509, 511, 512, 501; 514/413, 421, 418

[56] References Cited

U.S. PATENT DOCUMENTS 3,429,970  2/1969  Rudolf et al. ................. 514/703
3,541,154  11/1970  Schmialek et al. ............. 564/484
3,665,040  5/1972  Ruegg et al. ................. 568/687

FOREIGN PATENT DOCUMENTS 62-56489  3/1987  Japan .

OTHER PUBLICATIONS

Chem. Ber., vol. 100, pp. 591-604 Gompper et al. (1967).
Chem. Ber., vol. 52, pp. 542-544 Freund et al. (1919).
CA 95:56283y Structure-Activity . . . Chagas' disease. De Oliveria Filho et al., p. 187, 1981.
CA 43956s vol. 67. Alka(poly)enyl compounds.Brit. 973,014, Oct. 1964, p. 43954.
CA 102:6874j Polyprenyl . . . activity. Yamatsu et al. p. 625, Nov. 1982.
CA 104:50997s Isoprenoids. Eisai Co. Ltd. p. 51000 Dec. 1983.
CA 113:24272t Total Synthesis . . . hypotaurocyamine group.
Asao et al. p. 24264, Chem. Lett., 1984.

Primary Examiner—Mary C. Lee
Assistant Examiner—Joseph K. McKane
Attorney, Agent, or Firm—Nikaido, Marmelstein, Murray & Oram

[57] ABSTRACT

There are given disclosures on a polyisoprene compound of the formula

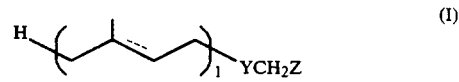
(I)

wherein Y is S, O, NH or

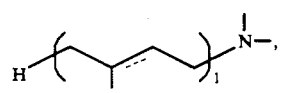

$l$ is an integer of 2–10, Z is a group of

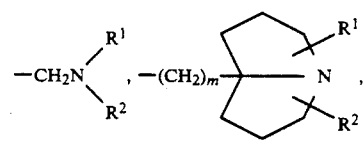

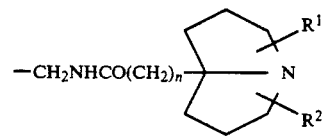

or

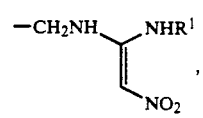

$R^1$ and $R^2$ are same or different and each means a hydrogen atom or an alkyl group having $C_{1-4}$, $m$ is an integer of 0 or 1, and $n$ is an integer of 0, 1 or 2, a salt thereof, a process for the preparation of same, and use thereof.

8 Claims, No Drawings

POLYISOPRENE COMPOUNDS AND SALTS THEREOF

BACKGROUND OF THE INVENTION

1. Field of the Invention

The present invention relates to novel polyisoprene compounds, salts thereof, process for the preparation thereof, and use thereof as a pharmaceutical composition to cure a digestive ulcer.

2. Related Arts

Medicines for curing the digestive ulcer have been, in general, classified into two groups of an inhibitor to offensive factors and another group of intensificator to defensive factors. Among them, the former type drugs have been greatly developed, and for instance, a drug of "Cimetidine" which is one of exemplar compounds in the group and one of antagonists to histamine $H_2$ receptor has provided such a great contribution of that it is excellent high curing ratio to the digestive ulcer, in comparison with other drugs to change a prior surgical treatment which has been mainly employed into an internal treatment administrating the drug.

As a result, various drugs such as "Ranitidine", "Famotidine" and the like have been developed, as antagonists to histamine $H_2$ receptors, other than said Cimetidine, so that a period of time for curing the digestive ulcer becomes shortened.

However, those drugs are inhibitors to offensive factors and its basis lies in inhibiting secretion of acid in the stomach. This means that if this type drug shows a strong inhibition, it also shows higher acid rebound, and therefor, it becomes such a serious problem that a relapse of the digestive ulcer may happen, when an administration of the drug was cheesed, in accordance with a diagnosis of that the disease has been cured.

In view of the problem on the inhibitor to offensive factors, in recent years, a development of the medicine for curing digestive ulcer has been directed to the latter group type drug, namely the intensificator to defensive factors.

Hitherto, drugs of "Gefarnate", "Cetraxate", "Teprenone" and the like have been developed, as the intensificators to defensive factors and have widely been employed for clinical treatment of the digestive ulcer, since those show a little side-effect and may be administered currently with another drug.

However, all of the latter type drugs do not show high anti-ulcer activity.

SUMMARY OF THE INVENTION

Therefore, a main object of the invention is to provide a compound and a salt thereof which belong to the group of intensificator to defensive factors, show powerful anti-ulcer activity, and do not cause a relapse of the ulcer, after cured thereof.

Additional, but important objects of the invention are provide a process for the preparation of the compound and salts thereof as well as a pharmaceutical composition which contains as an effective ingredient the compound or salt to cure the digestive ulcer.

The inventors have checked as to the known drugs of "Gefarnate" and "Teprenone" belonging to the intensificators to defensive factors, based on their attention to a polyisoprene skeleton as a basic structure of the drugs, and then they energetically studied and investigated as to a modification of the structure.

As a result, they have succeed in a synthesis of various polyisoprene compounds which show an action for intensificating the defensive factors, and show an anti-ulcer activity far excellent than that of the conventional intensificators to defensive factors, to establish the invention.

According to the invention, the problem in the prior arts can be dissolved and said main object can be attained by a polyisoprene compound of the formula

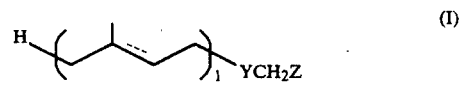
(I)

wherein Y is S, O, NH or

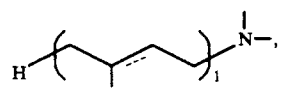

$l$ is an integer of 2-10, Z is a group of

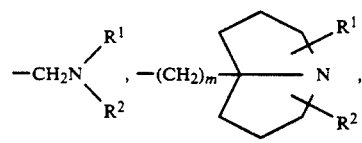

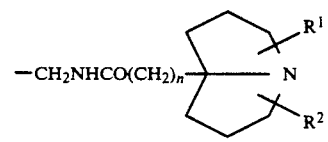

or

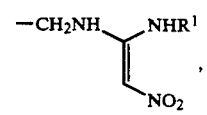

$R^1$ and $R^2$ are same or different and each means a hydrogen atom or an alkyl group having $C_{1-4}$, $m$ is an integer of 0 or 1, and $n$ is an integer of 0, 1 or 2, and a salt thereof.

In the compounds shown by Formula (I), the alkyl group having $C_{1-4}$ may be a straight-chain or branched-chain alkyl group. As the straight-chain alkyl radicals, methyl, ethyl, n-propyl, n-butyl and the like may be listed. As the branched-chain alkyl radicals, isopropyl, isobutyl, sec-butyl, tert-butyl and the like may be listed.

The salts according to the invention are, of course, non-toxic salts which can be pharmacologically accepted. As acids for forming the salts, hydrochloric acid, sulfuric acid, hydrobromic acid and the like mineral acids; and methanesulfonic acid, fumaric acid, maleic acid and the like organic acids can be listed.

Among the compounds shown by Formula (I), according to the invention, the compounds of the formula

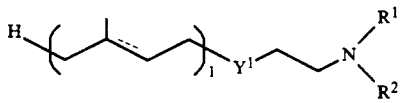

wherein $Y^1$ is sulfur atom; and $R^1$, $R^2$ and $l$ have the meanings as referred to,
and a salt thereof can be prepared by reacting in the presence of a base a compound of the formula

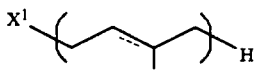

wherein X is a halogen atom and $l$ has the meaning as referred to,
with a compound of the formula

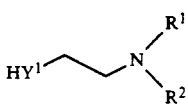

wherein $Y^1$, $R^1$ and $R^2$ have the meanings as referred to, and if necessary, converting the resulting compound into the salt.

The compound (IV) as raw material for said reaction can be prepared by halogenating a compound

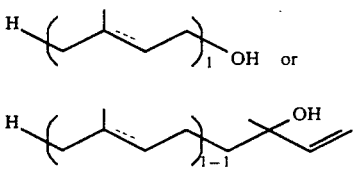

wherein $l$ has the meaning as referred to, which has been marketed. The halogenation can be carried out by stirring one of the compounds (III) and a halogenation agent in an inert solvent at −20° to 100° C. for 0.5 to 7 hours. As the halogenation agent, hydrogen halogenide, phosphorus halogenide (in the presence of pyridine or quinoline), triphenylphosphinecarbon tetrahalogenide, sulfonyl halogenide, sulfonium halogenide, and thionyl halogenide can be listed. It is preferable to carry out a bromination with phosphorus tribromide in the presence of pyridine or quinoline and a chlorination with triphenylphosphine-carbon tetrachloride. As the solvent, N,N-dimethylformamide, N,N-dimethylacetamide, dimethylsulfoxide, hexamethylphosphoric triamide or the like aprotic solvent, ethyl ether, dioxane, tetrahydrofuran or the like ether, benzene, toluene, xylene or the like aromatic hydrocarbon, carbon tetrachloride, n-hexane, petroleum ether or a mixture thereof can be employed.

As the base for the reaction between the compounds IV and V, sodium carbonate, potassium carbonate or the like alkali carbonate, sodium bicarbonate or the like alkali hydrogen carbonate, triethylamine, N,N-dimethyl aniline, pyridine, 1,8-azabicyclo[5.4.0]undec-7-ene or the like organic amine, sodium hydride, sodium amide or the like can be employed. In this case, if necessary, a condensation agent such as 18-crown-6 or the like crown ether may be added. As the base, it is preferable to use the 1,8-azabicyclo[5.4.0]undec-7-ene or sodium hydride (in the presence of the 18-crown-6). The reaction between the compounds iV and V can be carried out by dissolving the compounds in an inert solvent and stirring the solution for 2 to 24 hours at 0°-100° C., in the presence of said base. As the solvent, N,N-dimethylformamide, N,N-dimethylacetamide, dimethylsulfoxide, hexamethylphosphoric triamide or the like aprotic solvent, dioxane, tetrahydrofuran or the like ether, benzene, toluene, xylene or the like aromatic hydrocarbon, or a mixture thereof can be employed. A molar ratio of compounds IV, V and the base of about 1.0:1.0–1.5:1.0–1.5 is preferable.

Among the compounds shown by Formula I, the compounds of the formula

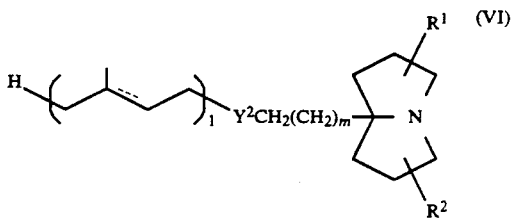

wherein $Y^2$ is hydrogen substituted nitrogen atom, $R^1$, $R^2$, $l$
and $m$ have the meanings as referred to, and a salt thereof can be prepared by reacting a compound of the formula

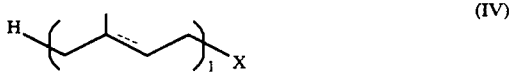

wherein $l$ and X have the meanings as referred to, with a compound of the formula

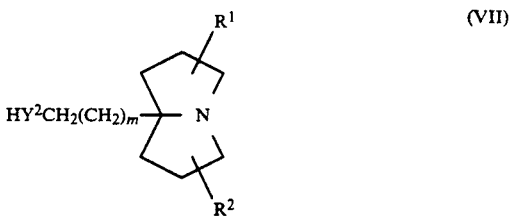

wherein $Y^2$, $R^1$, $R^2$ and $m$ have the meanings as referred to, and if necessary converting the resulting compound into the salt.

The reaction can be carried out by dissolving the compounds IV and VII into an inert solvent and stirring the solution for 2–24 hours at −20°–100° C. It is preferable to set a mol ratio (VII/IV) between the compounds as about 1.0–1.5, and more preferably as 1.2. As the solvent, N,N-dimethylformamide, N,N-dimethylacetamide, dimethylsulfoxide, hexamethylphosphoric triamide or the like aprotic solvent, ethyl ether, dioxane, tetrahydrofuran, or the like ether, benzene, toluene, xylene or the like aromatic hydrocarbon, methanol, ethanol or the like alcohol or a mixture thereof can be employed. If necessary, a base may be added in the reaction system. As the base, sodium carbonate, potassium carbonate or the like alkali carbonate, sodium bicarbonate or the like alkali hydrogen carbonate, triethylamine, N,N-dimethylaniline, pyridine, 1,8-azabicyclo[5.4.0]-undec-7-ene or the like organic amine, sodium hydride, sodium amide or the like can employed.

When the mol ratio (VII/IV) is set as about 2.0-3.0, following dimer can be obtained.

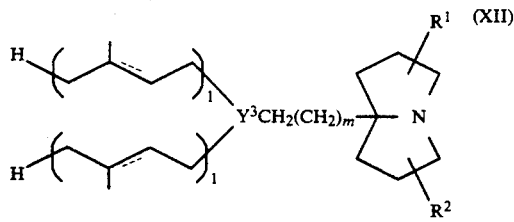

wherein $Y^3$ is a nitrogen atom, $R^1$, $R^2$, $l$ and $m$ have the meanings as referred to.

Conditions for the reaction, namely solvent, base and temperature are substantially same with those for the cases as referred to hereinbefore.

Among the compounds shown by Formula (I), the compounds of the formula

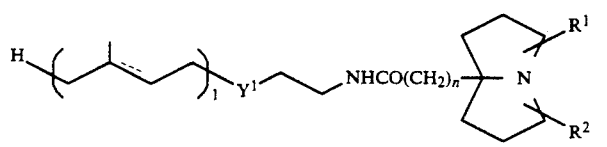

wherein $Y^1$, $R^1$, $R^2$, $l$ and $n$ have the meanings as referred to,
and a salt thereof can be prepared by reacting, in the presence of a base, a compound of the formula

wherein $Y^1$ and $l$ have the meanings as referred to, with a compound of the formula

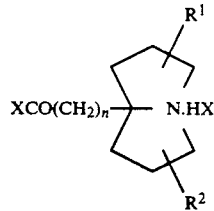

wherein $R^1$, $R^2$, X and $n$ have the meanings as referred to, and if necessary converting the resulting compound into the salt.

As the base for the reaction between the compounds IX and X, sodium carbonate, potassium carbonate or the like alkali carbonate, sodium bicarbonate or the like alkali hydrogen carbonate; triethylamine, N,N-dimethylaniline, pyridine or the like organic amine can be employed. The reaction between the compounds IX and X can be carried out by dissolving the compounds in an inert solvent, and stirring the solution for 1-24 hours at −20°-60° C., in the presence of the base. As the solvent, N,N-dimethylformamide, N,N-dimethylacetamide, dimethylsulfoxide, hexamethylphosphoric triamide or the like aprotic solvent, dioxane, tetrahydrofuran or the like ether, benzene, toluene, xylene or the like aromatic hydrocarbon, pyridine or a mixture thereof can be employed. It is preferable to react the compounds IX and X in the pyridine at 0°-30° C. One of the raw materials, namely the compound X can easily be synthesized in accordance with the method as disclosed in Jap. Pat. No. Sho 62-56489 (A)

Among the compounds shown by Formula I, the compound of the formula

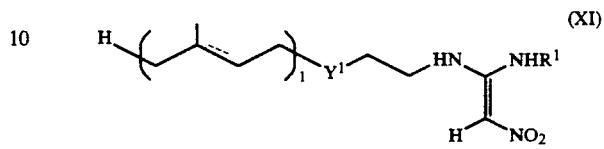

wherein $Y^1$, $R^1$ and $l$ have the meanings as referred to, and a salt thereof can be prepared by reacting a compound of the formula

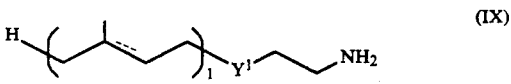

wherein $Y^1$ and $l$ have the meanings as referred to, with a compound of the formula

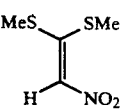

reacting the resulting compound of the formula

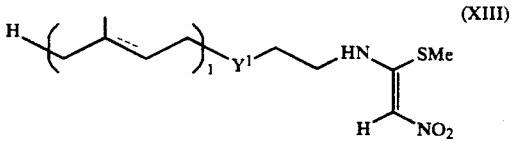

wherein $Y^1$ and $l$ have the meanings as referred to, with a compound of the formula

wherein $R^1$ has the meaning as referred to, and if necessary, converting the resulting compound into the salt.

The reaction between the compounds IX and XIII can be carried out by dissolving the compounds into an inert solvent, and stirring the solution for 1.0-8 hours at 20°-100° C. It is preferable to set a mol ratio of the compounds, as IX:XII=1.0:1.0-1.5. As the solvent, N,N-dimethylformamide, N,N-dimethylacetamide, dimethylsulfoxide, hexamethylphosphoric triamide or the like aprotic solvent, ethyl ether, dioxane, tetrahydrofuran or the like ether, benzene, toluene, xylene or the like aromatic hydrocarbon, methanol, ethanol or the like alcohol, acetonitrile, carbon tetrachloride, n-hexane, petroleum ether or a mixture thereof can be employed. One of the raw materials, namely the compound (XII) can easily be synthesized in accordance with known methods ["Chem. Ber.", Vol. 52, page 542 (1919) and "Chem. Ber.", Vol. 100, page 591 (1967)].

While, the reaction between the compounds XIII and XIV can be carried out by dissolving the compounds in an inert solvent or dissolving the compound XIII into the compound XIV, and stirring the solution for 0.1-5 hours at 0°-100° C. As the solvent, N,N-dimethylformamide, N,N-Dimethylacetamide, dimethylsulfoxide, hexamethylphosphoric triamide or the like aprotic solvent, ethyl ether, dioxane, tetrahydrofuran or the like ether, benzene, toluene, xylene or the like aromatic hydrocarbon, methanol, ethanol or the like alcohol, acetonitrile, or a mixture thereof can be employed.

FORM OF MEDICINE AND AMOUNT OF DOSAGE

When a medicine shall be prepared by using as an effective ingredient the compound or salt thereof according to the invention, there is no limitation in its form and therefore, it may take in a solid form such as a tablet, pill, capsule, powder, granule, suppository and the like; or a liquid form such as a solution, suspension, emulsion and the like. The medicine can be prepared in a conventional manner.

For preparing the solid type medicines, a starch, lactose, glucose, calcium phosphate, magnesium stearate, gum arabic or the like filler may be added. If necessary, conventional additives such as a lublicant, disintegrator, coating agent, coloring may also be used. While, for preparing the liquid type medicines, a stabilizer, solubilizing agent, suspending agent, emulsifier, buffer, preservative or the like may be employed.

An amount of dosage of the compound or salt according to the invention depends on various factors such as kind of same to be selected, form of the medicine, condition of illness, age of the patient, but on case for an adult, an amount of about 0.1-2000 mg/day and more particularly 10-150 mg/day is suitable.

EXAMPLES AND OTHERS

The invention will now be further explained with reference to Manufacturing Examples, Pharmacological Test Example and Medicine Preparation Examples.

EXAMPLE 1

2-(3,7,11,15,19,23,27,31,35-Nonamethyl-2,6,10,14,18,22,26,30,34-hexatriacontanonaen-1-ylthio)ethylamine a) 1-Chloro-3,7,11,15,19,23,27,31,35-nonamethyl-2,6,10,14,18,22,26,30,34-hexatriacontanonaene Under an atmosphere of argon, triphenylphosphine (29.7 g, 113 mmol) was added to a solution of 3,7,11,15,19,23,27,31,35-nonamethyl-2,6,10,14,18,22,26,30,34-hexatriacontanonaen-1-ol (54.9 g, 87.0 mmol) in 78 ml of carbon tetrachloride.

The mixture was heated at reflux temperature for 2.5 hours and cooled in an ice bath. To the reaction mixture, 90 ml of n-hexane were added. The resulting precipitate was filtered off and the filtrate was evaporated in vacuo to dryness. The remaining residue was treated as above (addition of n-hexane, filtration and evaporation) for purification to afford 54.0 g (95.4%) of the desired compound, as a brown oil.

TLC: Rf=0.34 (silica gel, n-hexane: AcOEt=5:1). IR spectrum ($v_{max}^{neat}$) cm$^{-1}$: 2980, 2930, 2860, 1670.

$^1$H-NMR spectrum (CDCl$_3$) δ ppm: 1.50-1.80 (30H, m, —CH$_3$×10), 1.90-2.40 (32H, m, —CH$_2$—×16), 4.13 (2H, d, J=8.0 Hz, —CH$_2$Cl), 4.90-5.40 (9H, m, C=CH—×9).

b) 2-(3,7,11,15,19,23,27,31,35-Nonamethyl-2,6,10,14,18,22,26,30,34-hexatriacontanonaen-1-ylthio)ethylamine Under an atmosphere of argon, sodium hydride (1.43 g, 35.8 mmol, 60% dispersion in mineral oil) was added to a solution of 2-aminoethanethiol (2.76 g, 35.8 mmol) in 90 ml of tetrahydrofuran. The mixture was heated at reflux temperature for 15 minutes and cooled in an ice bath. To the reaction mixture, 18-crown-6 (20 mg, 0.08 mmol) was added and then a solution of 1-chloro-3,7,11,15,19,23,27,31,35-nonamethyl-2,6,10,14,18,22,26,30,34-hexatriacontanonaene [23.2 g, 35.7 mmol, prepared as described in Item a) given above] in 90 ml of tetrahydrofuran was added in dropwise for 10 minutes. The reaction mixture was heated at reflux temperature for 4 hours and then cooled. After addition of water (1 ml), the solvent was evaporated in vacuo to dryness. The remaining residue was partitioned between water and n-hexane. The aqueous layer was extracted with n-hexane to combine the n-hexane layers. The combined organic layer was dried over anhydrous sodium sulfate, filtered and evaporated in vacuo to dryness. The remaining residue was chromatographed on silica gel, eluting with CH$_2$Cl$_2$/MeOH (50:1-20:1) to afford 15.1 g (61.3%) of the desired compound, as a pale brown oil.

TLC: Rf=0.47 (silica gel, CH$_2$Cl$_2$:MeOH=10:1). Mass spectrum (EI/DI) m/z: 689 (M+), 135 (base peak). IR spectrum ($v_{max}^{neat}$) cm$^{-1}$: 3350, 2960, 2920, 2850, 1660, 1570.

$^1$H-NMR spectrum (CDCl$_3$) δ ppm: 1.50-1.80 (30H, m, —CH$_3$×10), 1.90-2.40 (32H, m, —CH$_2$—×16), 2.40-3.10 (4H, m, H$_2$NCH$_2$CH$_2$S—), 3.20 (2H, d, J=8.0 Hz, =CHCH$_2$S—), 5.00-5.40 (9H, m, —C=CH—×9).

EXAMPLE 2

2-(3,7,11,15-Tetramethyl-2-hexadecaen-1-ylthio)ethylamine a) Phytyl chloride (1-chloro-3,7,11,15-tetramethyl-2-hexadecaene)

The procedure described in Example 1-a) was repeated except that phytol (3,7,11,15-tetramethyl-2-hexadecaen-1-ol (25.8 g, 87.2 mmol) was employed as the starting material in place of 3,7,11,15,19,23,27,31,35-nonamethyl-2,6,10,14,18,22,26,30,34-hexatriacontanonaen-1-ol, to afford 24.1 g (88.0%) of the desired compound, as a brown oil.

b) 2-(3,7,11,15-Tetramethyl-2-hexadecaen-1-ylthio)ethylamine

Under an atmosphere of argon, sodium hydride (9.60 g, 240 mmol, 60% dispersion in mineral oil) was added to a solution of 2-aminoethanethiol (15.3 g, 200 mmol) in 200 ml of tetrahydrofuran and the mixture was stirred at 20° C. for 30 minutes. To the reaction mixture, 18-crown-6 (50 mg, 0.190 mmol) was added and then a solution of phytyl chloride (1-chloro-3,7,11,15-tetramethyl-2-hexadecaene) [55.0 g, 175 mmol, prepared as described in Item a) given above] in 200 ml of tetrahydrofuran was added in dropwise for an hour at below 10° C. After stirring at 20°-30° C. for 24 hours, water was added to the reaction mixture until forming did not occur. The solvent was evaporated in vacuo to dryness and the remaining residue was extracted with ethyl ether. The ether layer was washed twice with water and an aqueous solution saturated with sodium chloride, dried over anhydrous sodium sulfate, filtered and evaporated in vacuo to dryness. The remaining residue was chromatographed on silica gel, eluting with $CH_2Cl_2/MeOH$ (10:1) to afford 50.9 g (81.8%) of the desired compound, as a pale brown oil.

Mass spectrum (EI/DI) m/z: 355 (M+), 77 (base peak). IR spectrum ($v_{max}^{neat}$) cm$^{-1}$: 3350, 2910, 2840, 1460.

$^1$H-NMR spectrum (CDCl$_3$) δ ppm: 0.83 (6H, s, —CH$_3$×2), 0.93 (6H, s, —CH$_3$×2), 1.03–1.60 (16H, br, —CH$_2$—×8), 1.60 (2H, s, —NH$_2$), 1.60–1.80 (5H, m, —CH$_3$, —CH$_2$—), 1.80–2.23 (3H, br, —CH—×3), 2.43–3.03 (4H, m, —SCH$_2$CH$_2$NH$_2$), 3.18 (2H, d, J=8.0 Hz, C=CHCH$_2$S—), 5.30 (1H, t, J=8.0 Hz, C=CHCH$_2$S—).

EXAMPLE 3

2-(3,7-Dimethyl-2,6-octadien-1-ylthio)ethylamine a) Geranyl chloride (1-chloro-3,7-dimethyl-2,6-octadiene)

The procedure described in Example 1-a) was repeated except that gelaniol (3,7-dimethyl-2,6-octadien-1-ol, 13.4 g, 87.0 mmol) was employed as the starting material in place of 3,7,11,15,19,23,27,31,35-nonamethyl-2,6,10,14,18,22,26,30,34-hexatriacontanonaen-1-ol, to afford 13.7 g (91.3%) of the desired compound, as a brown oil.

b) 2-(3,7-Dimethyl-2,6-octadien-1-ylthio)ethylamine

The procedure described in Example 2-b) was repeated excepted that geranyl chloride [1-chloro-3,7-dimethyl-2,6-octadiene, 30.2 g, 175 mmol, prepared as described in Item a)] was employed as the starting material in place of phytyl chloride (1-chloro-3,7,11,15-tetramethyl-2-hexadecaene), to afford 30.6 g (82.0%) of the desired compound, as a pale brown oil.

Mass spectrum (EI/DI) m/z: 213 (M+), 69 (base peak).

IR spectrum ($v_{max}^{neat}$) cm$^{-1}$: 3360, 2950, 2910, 2850, 1660.

$^1$H-NMR spectrum (CDCl$_3$) δ ppm: 1.47 (2H, s, —NH$_2$), 1.60–1.80 (9H, m, —CH$_3$×3), 2.00–2.30 (4H, m, —CH$_2$—×2), 2.46–3.09 (4H, m, —SCH$_2$CH$_2$NH$_2$) 3.20 (2H, d, J=7.0 Hz, C=CHCH$_2$S—), 5.00–5.50 (2H, m, =CHCH$_2$—×2).

EXAMPLE 4

2-(3,7,11,15,19,23,27,31,35,39-Decamethyl-2,6,10,14,18,22,26,30,34,38-tetracontadecaen-1-ylthio)ethylamine a) 1-Bromo-3,7,11,15,19,23,27,31,35,39-decamethyl-2,6,10,14,18,22,26,30,34,38-tetracontadecaene Under an atmosphere of argon, a solution of phosphorus tribromide (8.32 g, 30.7 mmol) in 27 ml of n-hexane was added in dropwise to a mixture of 3,7,11,15,19,23,27,31,35,39-decamethyl-2,6,10,14,18,22,26,30,34,38-tetracontadecaen-1-ol (40 g, 57.3 mmol) and pyridine (1.92 ml, 23.8 mmol) in 587 ml of n-hexane at the temperature below 10° C. The solution was stirred at 10° C. for an hour, allowed to warm slowly from 10° to 20° C., stirred at 20°–25° C. for an hour and poured into cracked ice with stirring. The resulting precipitate was filtered off and the filtrate was extracted with n-hexane. The organic layer was washed with 5% sodium bicarbonate aqueous solution, dried over anhydrous sodium sulfate, filtered and evaporated in vacuo to dryness to afford 39.5 g (90.4%) of the desired compound, as a yellow oil.

TLC: Rf=0.34 (silica gel, n-hexane:AcOEt=5:1). IR spectrum ($v_{max}^{neat}$) cm$^{-1}$: 2980, 2940, 1670.

$^1$H-NMR spectrum (CDCl$_3$) δ ppm: 1.60–2.15 (69H, m, —CH$_3$×11, —CH$_2$—×18), 4.03 (2H, d, J=8.3 Hz, —CH$_2$Br), 5.09–5.14 (9H, m, =CHCH$_2$CH$_2$—×9), 5.53 (1H, t, J=8.3 Hz, =CHCH$_2$Br).

b) 2-(3,7,11,15,19,23,27,31,35,39-Decamethyl-2,6,10,14,18,22,26,30,34,38-tetracontadecan-1-ylthio)ethylamine Under an atmosphere of argon, a solution of 1-bromo3,7,11,15,19,23,27,31,35,39-decamethyl-2,6,10,14,18,22,26,30,34,38-tetracontadecaene [20.0 g, 26.3 mmol, prepared as described in Item a)] in 100 ml of benzene was added in dropwise to a mixture of 1,8-diazabicyclo[5.4.0]undec-7-ene (DBU, 4.0 g, 26.3 mmol) and 2-aminoethanethiol (2.43 g, 31.6 mmol) in 200 ml of benzene at 15° C. After stirring for 18 hours at 20°–25° C., the resulting precipitate was filtered and washed with ethyl ether. The washings were combined with the filtrate, poured into cracked ice with stirring. The solution was extracted with ethyl ether. The organic layer was dried over anhydrous sodium sulfate, filtered and evaporated in vacuo to dryness. The remaining residue, as a brown oil was chromatographed on silica gel, eluting with $CH_2Cl_2$/MeOH (10:0–10:1) to afford 12.0 g (86.3%) of the desired compound, as a yellow oil.

Mass spectrum (EI/DI) m/z: 757 (M+, base peak), 280, 203, 135, 81, 69. IR spectrum ($v_{max}^{neat}$) cm$^{-1}$: 3350, 2950, 2910, 2850, 1660.

$^1$H-NMR spectrum (CDCl$_3$) δ ppm: 1.60–2.15 (71H, m, —CH$_3$×11, —CH$_2$—×18, —NH$_2$), 2.58 (2H, t, J=6.4 Hz, —SCH$_2$CH$_2$NH$_2$) 2.87 (2H, t, J=6.4 Hz, —SCH$_2$CH$_2$NH$_2$), 3.15 (2H, d, J=7.8 Hz, =CHCH$_2$S—), 5.05–5.15 (9H, m, =CHCH$_2$—×9), 5.25 (1H, t, J=7.8 Hz, =CHCH$_2$S—).

EXAMPLE 5

2-(3,7,11,15-Tetramethyl-2,6,10,14-hexadecatetraen-1-ylthio)ethylamine a) 1-Bromo-3,7,11,15-tetramethyl-2,6,10,14-hexadecatetraene The procedure described in Example 4-a) was repeated except that 3,7,11,15-tetramethyl-1,6,10,14-hexadecatetraen-3-ol (16.6 g, 57.2 mmol) was employed as the starting material in place of 3,7,11,15,19,23,27,31,35,39-decamethyl-2,6,10,14,18,22,26,30,34,38-tetracontadecaen-1-ol, to afford 20.2 g (quant.) of the desired compound, as a yellow oil.

Mass spectrum (EI/DI) m/z: 352 (M+), 272, 203, 149, 107, 93, 81, 69 (base peak).

$^1$H-NMR spectrum (CDCl$_3$) δ ppm: 1.60–2.15 (27H, m, —CH$_3$×5, —CH$_2$—×6), 4.03 (2H, d, J=8.2 Hz, —CH$_2$Br), 5.05–5.16 (3H, m, =CHCH$_2$CH$_2$×3), 5.53 (1H, t, J=8.2 Hz, =CHCH$_2$Br), b) 2-(3,7,11,15-Tetramethyl-2,6,10,14-hexadecatetraen-1-ylthio)ethylamine The procedure described in Example 4-b) was repeated except that 1-bromo-3,7,11,15-tetramethyl-2,6,10,14-hexadecatetraene [9.3 g, 26.3 mmol, prepared as described in Item a)] was employed as the starting material in place of 1-bromo-3,7,11,15,19,23,27,31,35,39-decamethyl- 2,6,10,14,18,22,26,30,34,38-tetracontadecaene, to afford 6.5 g (70.7%) of the desired compound, as a yellow oil.

Mass spectrum (EI/DI) m/z: 349 (M+), 280, 203, 135, 107, 93, 81, 69 (base peak). IR spectrum ($v_{max}^{neat}$) cm$^{-1}$: 3360, 2950, 2920, 2860, 1460.

$^1$H-NMR spectrum (CDCl$_3$) δ ppm: 1.60–2.17 (29H, m, —CH$_3$×5, —CH$_2$—×6, —NH$_2$), 2.59 (2H, t, J=6.4 Hz, —SCH$_2$CH$_2$N—), 2.88 (2H, t, J=6.4 Hz, —SCH$_2$CH$_2$NH$_2$), 3.14 (2H, d, J=7.8 Hz, —CH$_2$CH$_2$S—), 5.07–5.15 (3H, m, =CHCH$_2$CH$_2$—×3), 5.24 (1H, t, J=7.8 Hz, =CHCH$_2$S—).

EXAMPLE 6

2-(3,7,11-Trimethyl-2,6,10-dodecatrien-1-ylthio)ethylamine a) 1-Bromo-3,7,11-trimethyl-2,6,10-dodecatriene The procedure in Example 4-a) was repeated except that 3,7,11-trimethyl-2,6,10-dodecatrien-1-ol (12.7 g, 57.3 mmol) was employed as the starting material in place of 3,7,11,15,19,23,27,31,35,39-decamethyl-2,6,10,14,18,22,26,30,34,38-tetracontadecaen-1-ol, to afford 15.8 g (96.9%) of the desired compound, as a yellow oil.

b) 2-(3,7,11-Trimethyl-2,6,10-dodecatrien-1-ylthio)ethylamine

The procedure in Example 4-b) was repeated except that 1-bromo-3,7,11-trimethyl-2,6,10-dodecatriene [7.5 g, 26.3 mmol, prepared by said Item b)] was employed as the starting material in place of 1-bromo-3,7,11,15,19,23,27,31,39-decamethyl-2,6,10,14,18,22,26,30,34,38-tetracontadecaene, to afford 5.5 g (74.3%) of the desired compound, as a pale yellow oil.

Mass spectrum (EI/DI) m/z: 281 (M+), 96 (base peak). IR spectrum ($v_{max}^{neat}$) cm$^{-1}$: 3370, 3300, 1442, 1223.

$^1$H-NMR spectrum (CDCl$_3$) δ ppm: 1.44–1.69 (12H, s, —CH$_3$×4), 1.95–2.15 (8H, m, —CH$_2$—×4), 2.56–2.61 (2H, m, —SCH$_2$CH$_2$NH$_2$), 2.86 (2H, t, J=6.3 Hz, —SCH$_2$CH$_2$NH$_2$), 3.15 (2H, d, J=7.8 Hz, =CHCH$_2$S—), 5.10 (2H, t, J=5.9 Hz, =CHCH$_2$CH$_2$—×2), 5.24 (1H, t, J=7.8 Hz, =CHCH$_2$S—).

EXAMPLE 7

2-Methylamino-1-nitro-2-[2-(3,7,11,15-tetramethyl-2,6,10,14-hexadecatetraen-1-ylthio)ethylamino]ethylene a) 2-Methylthio-1-nitro-2-[2-(3,7,11,15-tetramethyl-2,6,10,14-hexadecatetraen-1-ylthio)ethylamino]ethylene A mixture of 2-(3,7,11,15-tetramethyl-2,6,10,14-hexadecatetraen-1-ylthio)ethylamine (14.0 g, 40.0 mmol, prepared as described in Example 5) and 1,1-bis(methylthio)-2-nitroethylene (6.60 g, 40.0 mmol) in 100 ml of acetonitrile was heated at reflux temperature for 5 hours. The reaction mixture was evaporated in vacuo to dryness and the remaining residue was chromatographed on silica gel, eluting with CHCl$_3$/MeOH (200:1) to afford 14.7 g (78.6%) of the desired compound, as a pale yellow oil.

Mass spectrum (EI/DI) m/z: 449 (M+), 69 (base peak). IR spectrum ($v_{max}^{neat}$) cm$^{-1}$: 2960, 2920, 2850, 1565.

$^1$H-NMR spectrum (CDCl$_3$) δ ppm: 1.60–1.87 (15H, m, —CH$_3$×5), 1.97–2.35 (12H, m, —CH$_2$—×6), 2.48 (3H, s, —SMe), 2.80 (2H, t, J=6.5 Hz, —SCH$_2$CH$_2$NH—), 3.27 (2H, d, J=7.5 Hz, =CHCH$_2$S—), 3.85 (2H, q, J=6.5 Hz, —SCH$_2$CH$_2$NH—), 4.95–5.53 (4H, m, =CH—×4), 6.66

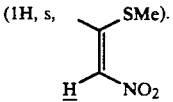

b) 2-Methylamino-1-nitro-2-[2-(3,7,11,15-tetramethyl-2,6,10,14-hexadecatetraen-1-ylthio)ethylamino]ethylene 2-Methylthio-1-nitro-2-[2-(3,7,11,15-tetramethyl-2,6,10,14-hexadecatetraen-1-ylthio)ethylamino]ethylene [12.5 g, 26.8 mmol, prepared as described in Item a)] was dissolved in 40% methylamine solution (134 ml, 1.34 mol, 40% methanol solution) and stirred at 20° C. for 30 minutes. The reaction mixture was evaporated in vacuo to dryness. The remaining residue was chromatographed on silica gel, eluting with CH$_2$Cl$_2$/MeOH (30:1) to afford 11.6 g (96.7%) of the desired compound, as a pale yellow oil.

Mass spectrum (EI/DI) m/z: 432 (M+), 69 (base peak). IR spectrum ($v_{max}^{neat}$) cm$^{-1}$: 2980, 2920, 2850, 1570.

$^1$H-NMR spectrum (CDCl$_3$) δ ppm: 1.62–1.85 (15H, m, —CH$_3$×5), 1.93–2.35 (12H, m, —CH$_2$—×6), 2.50–3.70 (7H, m, —NHMe, —SCH$_2$CH$_2$NH—), 3.25 (2H, d, J=8.0 Hz, =CHCH$_2$S—), 4.90–5.53 (4H, m, =CHCH$_2$×4), 5.90–7.30 (1H, br, —NH—), 6.70

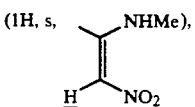

9.90–10.70 (1H, br, —NH—).

EXAMPLE 8

5-{[(3,7,11,15,19,23,27,31,35,39-Decamethyl-2,6,10,14,18,22,26,30,34,38-tetracontadecaen-1-yl)amino]methyl}-1-azabicyclo[3.3.0]octane Under an atmosphere of argon, a solution of 1-bromo-3,7,11,15,19,23,27,31,35,39-decamethyl-2,6,10,14,18,22,26,30,34,38-tetracontadecaene [8.00 g, 10.5 mmol, prepared as described in Example 4-a)] in 48.0 ml of benzene was added in dropwise to a solution of 5-aminomethyl-1-azabicyclo-[3.3.0]octane (1.76 g, 12.6 mmol) in 48.0 ml of benzene at 15° C. and the resulting solution was stirred at 50° C. for 5 hours. The solvent in the reaction mixture was evaporated in vacuo to dryness and the remaining residue was partitioned between chloroform and 10% sodium hydroxide aqueous solution. The organic layer was washed with saturated sodium chloride aqueous solution, dried over anhydrous sodium sulfate, filtered and evaporated in vacuo to dryness to give a brown residue. The residue was chromatographed on silica gel, eluting with CH$_2$Cl$_2$/MeOH (10.0:0–10:1.5) to afford 4.4 g (51.1%) of the desired compound, as colorless crystals.

Melting point: 59°–61° C. Mass spectrum (EI/DI) m/z: 820 (M+), 110 (base peak). IR spectrum ($v_{max}^{KBr}$) cm$^{-1}$: 2912, 1660.

¹H-NMR spectrum (CDCl₃) δ ppm: 1.60-2.19 (77H, m, —CH₃×11, —CH₂—×18, 8H of 1-azabicyclo[3.3.-0]octane), 2.74-2.87 (2H, m, 2H of 1-azabicyclo[3.3.-0]octane), 2.83 (2H, s, —NHCH₂—), 3.30 (2H, d, J=6.4 Hz, =CHCH₂NH—) 3.58-3.64 (2H, m, 2H of 1-azabicyclo[3.3.0]octane), 5.11 (9H, m, =CHCH₂CH₂—×9), 5.23 (1H, t, J=6.4 Hz, =CHCH₂NH—).

TLC: Rf=0.47 [silica gel, CH₂Cl₂: MeOH=5:1 (v/v)].

EXAMPLE 9

5-{[(3,7,11,15-Tetramethyl-2,6,10,14-hexadecatetraen-1-yl)amino]methyl}-1-azabicyclo[3.3.0]octane Under an atmosphere of argon, a solution of 1-bromo-3,7,11,15-tetramethyl-2,6,10,14-hexadecatetraene [6.90 g, 19.5 mmol, prepared as described in Example 5-a)] in 138 ml of ethanol was added in dropwise to a solution of 5-aminomethyl-1-azabicyclo[3.3.0]octane (3.3 g, 23.6 mmol) in 35 ml of ethanol at the temperature below 0° C. The reaction mixture was allowed to warm slowly from 0°-20° C. and then stirred at 20°-25° C. for 5 hours. The resulting solution was treated as described in Example 8 to afford 4.0 g (49.8%) of the desired compound, as a pale brown oil.

Mass spectrum (EI/DI) m/z: 412 (M⁺), 110 (base peak). IR spectrum ($\nu_{max}^{neat}$) cm⁻¹: 2922, 1660.

¹H-NMR spectrum (CDCl₃) δ ppm: 1.50-2.30 (35H, m, —CH₃×5, —CH₂—×6, 8H of 1-azabicyclo[3.3.-0]octane), 2.81-2.90 (2H, m, 2H of 1-azabicyclo[3.3.0]octane), 2.88 (2H, s, —NHCH₂—), 3.31 (2H, d, J=6,8 Hz,=CHCH₂NH—), 3.63-3.72 (2H, m, 2H of 1-azabicyclo[3.3.0]octane), 5.10 (3H, m, =CHCH₂CH₂—×3), 5.24 (1H, t, J=6.8 Hz,=CHCH₂NH—).

TLC: Rf=0.40 [silica gel, CH₂Cl₂: MeOH=5:1(V/V)].

EXAMPLE 10

N-[2-(3,7,11,15,19,23,27,31,35,39-Decamethyl-2,6,10,14,18,22,26,30,34,38-tetracontadecaen-1-ylthio)ethyl]-(1-azabicyclo[3.3.0]octan-5-yl)acetamide (1-Azabicyclo[3.3.0]octan-5-yl)acetyl chloride hydrochloride (2.00 g, 8.93 mmol) was added to a solution of 2-(3,7,11,15,19,23,27,31,35,39-decamethyl-2,6,10,14,18,22,26,30,34,38-tetracontadecaen-1-ylthio)ethylamine (5.00 g, 6.61 mmol, prepared as described in Example 4) in 75 ml of pyridine at the temperature below 20° C. and the solution was stirred at 25° C. for 3 hours. (1-Azabicyclo[3.3.0]octan-5-yl)acetyl chloride hydrochloride (0.9 g, 4.02 mmol) was further added to the reaction mixture at the temperature below 20° C. and the solution was stirred at 25° C. for an hour. The solvent in the reaction mixture was evaporated in vacuo to dryness and the remaining residue was partitioned between chloroform and 10% sodium hydroxide aqueous solution. The organic layer was washed with saturated sodium chloride aqueous solution, dried over anhydrous sodium sulfate, filtered and evaporated in vacuo to dryness to give a brown residue. The residue was chromatographed on silica gel, eluting with CH₂Cl₂/MeOH (10:0-10:1.5) to afford 5.2 g (86.7%) of the desired compound, as a colorless oil.

Mass spectrum (EI/DI) m/z: 908 (M⁺), 680, 227, 110 (base peak). IR spectrum ($\nu_{max}^{neat}$) cm⁻¹: 2910, 1670.

¹H-NMR spectrum (CDCl₃) δ ppm: 1.60-2.11 (77H, m, —CH₃×11, —CH₂—×18, 8H of 1-azabicyclo[3.3.-0]octane), 2.34 (2H, s, —COCH₂—), 2.58-2.71 (4H, m, —SCH₂CH₂NH—, 2H of 1-azabicyclo[3.3.0]octane), 3.09-3.19 (4H, m, =CHCH₂S—, 2H of 1-azabicyclo[3.3.0]octane), 3.39-3.46 (2H, m, —SCH₂CH₂NH—), 5.11 (9H, m, =CHCH₂CH₂—×9), 5.23 (1H, t, J=7.8 Hz, =CHCH₂S—), 8.81 (1H, brs, —NHCO—).

TLC: Rf=0.44 [silica gel, CH₂Cl₂: MeOH=5:1 (v/v)].

EXAMPLE 11

N-[2-(3,7,11,15-Tetramethyl-2,6,10,14-hexadecatetraen-1-ylthio)ethyl]-(1-azabicyclo[3.3.0]octan-5-yl)acetamide The procedure described in Example 10 was repeated except that 2-(3,7,11,15-tetramethyl-2,6,10,14-hexadecatetraen-1-ylthio)ethylamine (2.30 g, 6.61 mmol, prepared as described in Example 5) was employed as the starting material in place of 2-(3,7,11,15,19,23,27,31,35,39-decamethyl-2,6,10,14,18,22,26,30,34,38-tetracontadecaen-1-ylthio)ethylamine, to afford 2.67 g (80.9%) of the desired compound, as a pale brown oil.

Mass spectrum (EI/DI) m/z: 500 (M⁺), 227, 196, 110 (base peak). IR spectrum ($\nu_{max}^{neat}$) cm⁻¹: 2910, 1670.

¹H-NMR spectrum (CDCl₃) δ ppm: 1.60-2.10 (35H, m, —CH₃×5, —CH₂—×6, 8H of 1-azabicyclo[3.3.-0]octane), 2.34 (2H, s, —COCH₂—), 2.58-2.71 (4H, m, —SCH₂CH₂NH—, 2H of 1-azabicyclo[3.3.0]octane), 3.08-3.19 (4H, m, =CHCH₂S—, 2H of 1-azabicyclo[3.3.0]octane), 3.39-3.46 (2H, m, —SCH₂CH₂NH—), 5.10 (3H, m, =CHCH₂CH₂—×3), 5.24 (1H, t, J=7.8 Hz, =CHCH₂S—), 8.81 (1H, brs, —NHCO—).

TLC: Rf=0.40 [silica gel, CH₂Cl₂: MeOH=5:1 (v/v)].

EXAMPLE 12

5-{[Bis(3,7,11,15-tetramethyl-2,6,10,14-hexadecatetraen-1-yl)amino]methyl}-1-azabicyclo[3.3.0]octane Under an atmosphere of argon, a solution of 5-aminomethyl-1-azabicyclo[3.3.0]octane (2.0 g, 14.3 mmol) and triethylamine (2.86 g, 28.3 mmol) in 50 ml of benzene was added in dropwise to a solution of 1-bromo-3,7,11,15-tetramethyl-2,6,10,14-hexadecatetraene [10.0 g, 28.3 mmol, prepared as described in Example 5-a)] in 50 ml of benzene at 15° C. The reaction mixture was allowed to warm slowly from 15°-22° C. and then stirred at 22°-25° C. for 5 hours. The reaction mixture was treated as described in Example 8 to afford 2.7 g (21.9%) of the desired compound, as a pale brown oil.

Mass spectrum (EI/DI) m/z: 684 (M⁺), 411, 110 (base peak).

IR spectrum ($\nu_{max}^{neat}$) cm⁻¹: 2910, 1660.

¹H-NMR spectrum (CDCl₃) δ ppm: 1.60-2.37 (62H, m, —CH₃×10, —CH₂—×12, 8H of 1-azabicyclo[3.3.-0]octane), 2.85-2.95 (4H, m, —NCH₂—, 2H of 1-azabicyclo[3.3.0]octane), 3.18 (4H, d, J=7.3 Hz, =CHCH₂N—×2), 3.78-3.88 (2H, m, 2H of 1-azabicyclo[3.3.0]octane), 5.10 (6H, m, =CHCH₂CH₂—×6), 5.23 (2H, m, =CHCH₂N—×2).

TLC: Rf=0.47 [silica gel, CH₂Cl₂: MeOH=5:1 (v/v)].

Pharmacological Test Example (Anti-ulcer activity)

Some polyisoprene compounds according to the invention were tested to evaluate their anti-ulcer activity in comparison with Teprenone and Gefarnate as controls, in accordance with the procedure proposed by Takagi et al ["Japan. J. Pharmacol.", Vol. 18, page 9 (1968)].

Male Sprague-Dawley rats were used, each having the body weight of 183.9 to 234.5 g. The animals were deprived of food for 24 hours prior to the test. They were immobilized in a restraint cage and immersed for 7 hours to the height of the xiphoid process in a water-bath kept at 23°±1° C. After inflation with 10 ml of 1% formalin, the isolated stomach was opened along the greater curvature. The ulcer index was determined as the sum of length (mm) of each erosion per rat. The compounds were administered orally 30 minutes before the restraint.

Results are shown in following Table 1 in terms of percent inhibition of anti-ulcer activity. In the Table, $ED_{50}$ represents the dose of test compound which gives 50% inhibition.

It is apparent from the results given in the Table that the compounds according to the invention have intensive activity on stress-induced gastric ulcer.

TABLE 1

| Compounds | Dose (mg/kg) | Number of animals | Inhibition (%) | $ED_{50}$ (mg/kg) |
|---|---|---|---|---|
| Example 1 | 12.5 | 10 | −3.1 | 39.7 |
| | 25 | 10 | 39.7 | |
| | 50 | 10 | 55.1 | |
| Example 2 | 12.5 | 10 | 9.0 | 30.8 |
| | 25 | 10 | 45.0 | |
| | 50 | 10 | 69.0 | |
| Example 3 | 50 | 10 | 13.3 | >50 |
| Example 4 | 12.5 | 10 | 11.1 | >50 |
| | 25 | 10 | 24.2 | |
| | 50 | 10 | 44.4 | |
| Example 5 | 12.5 | 10 | −2.8 | 21.1 |
| | 25 | 10 | 57.4 | |
| | 50 | 10 | 88.0 | |
| Example 6 | 50 | 10 | 15.4 | >50 |
| Example 7 | 12.5 | 10 | −7.0 | 37.4 |
| | 25 | 10 | 23.8 | |
| | 50 | 10 | 67.8 | |
| Example 8 | 50 | 10 | 10.3 | >50 |
| Example 9 | 12.5 | 10 | 38.4 | 16.6 |
| | 25 | 10 | 67.9 | |
| | 50 | 10 | 84.9 | |
| Example 10 | 12.5 | 10 | 27.3 | >50 |
| | 25 | 10 | 33.9 | |
| Example 11 | 12.5 | 10 | 9.4 | 26.0 |
| | 25 | 10 | 51.0 | |
| | 50 | 10 | 68.5 | |
| Example 12 | 12.5 | 9 | 21.5 | ≧25.0 |
| | 25 | 10 | 50.0 | |
| Teprenone | 25 | 10 | 0.0 | >100 |
| | 50 | 10 | 9.4 | |
| | 100 | 9 | 48.3 | |
| Gefarnate | 100 | 10 | 24.6 | 387.3 |
| | 200 | 10 | 19.2 | |
| | 400 | 10 | 51.5 | |

Medicine Preparation Example 1 (Tablet)

Following ingredients were mixed and treated in a conventional manner to prepare tablets.

| Ingredients | |
|---|---|
| Product of Example 9 | 10.0 (mg) |
| Corn starch | 20.0 |
| Purified sucrose | 40.0 |
| Carboxymethyl cellulose calcium salt | 20.0 |
| Microcrystalline cellulose | 80.0 |
| Polyvinylpyrrolidone | 10.0 |
| Talc | 20.0 |
| | 200.0 mg/tablet |

Medicine Preparation Example 2 (Capsule)

Following ingredients were mixed and treated in a conventional manner to prepare capsules.

| Ingredients | |
|---|---|
| Product of Example 5 | 10.0 (mg) |
| Microcrystalline cellulose | 120.0 |
| Corn starch | 30.0 |
| Lactose | 34.0 |
| Polyvinylpyrrolidone | 6.0 |
| | 200.0 mg/capsule |

Medicine Preparation Example 3 (Granule)

Following ingredients were mixed and treated in a conventional manner to prepare granules.

| Ingredients | |
|---|---|
| Product of Example 11 | 10.0 (mg) |
| Microcrystalline cellulose | 210.0 |
| Corn starch | 280.0 |
| | 500.0 mg/wrapper |

Medicine Preparation Example 4 (Injection)

An injection was prepared in a conventional manner with use of following ingredients and under sterile condition.

| Ingredients | |
|---|---|
| Product of Example 9 (hydrochloride) | 2.0 (mg) |
| Sodium chloride | 8.0 |
| Distilled water | suitable amount |
| | 1.0 ml/vial |

We claim:

1. A polyisoprene compound of the formula

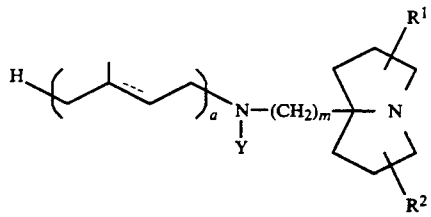

wherein Y is a hydrogen atom or a group of

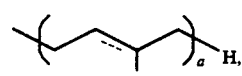

a is an integer of 2–10, $R^1$ and $R^2$ are the same or different and each means a hydrogen atom or an alkyl group having, $C_{1-4}$ and m is an integer of 1 or 2, and a salt thereof.

2. A polyisoprene compound and a salt thereof as claimed in claim 1, wherein said compound is selected from the group consisting of a) 5-{[(3,7,11,15-tetramethyl-2,6,10,14-hexadecatetraen-1-yl)amino]methyl}-1-azabicyclo[3.3.0]octane;

b) 5-{[(3,7,11,15,19,23,27,31,35,39-decamethyl-2,6,10,14,18,22,26,30,34,38-tetracontadecaen-1-yl)amino]methyl}-1-azabicyclo[3.3.0]octane; and c) 5-{[bis(3,7,11,15-tetramethyl-2,6,10,14-hexadecatetraen-1-yl)amino]methyl}-1-azabicyclo[3.3.0]octane.

3. A polyisoprene compound of the formula

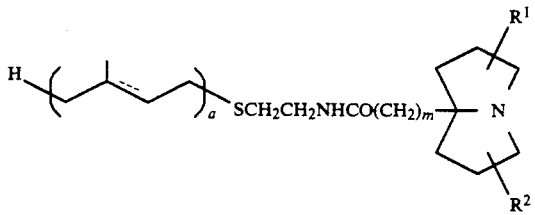

wherein a is an integer of 2–10, $R^1$ and $R^2$ are the same or different and each means a hydrogen atom or an alkyl group having $C_{1-4}$ and m is an integer of 0 or 1, and a salt thereof.

4. A polyisoprene compound and a salt thereof as claimed in claim 3, wherein said compound is selected from the group consisting of a) N-[2-(3,7,11,15-tetramethyl-2,6,10,14-hexadecatetraen-1-ylthio)ethyl]-(1-azabicyclo[3.3.0]octan-5-yl)acetamide; and b) N-[2-(3,7,11,15,19,23,27,31,35,39-decamethyl-2,6,10,14,18,22,26,30,34,38-tetraconta-decaen-1-ylthio)ethyl]-(1-azabicyclo[3.3.0]octan-5-yl)acetamide.

5. A pharmaceutical composition for curing a digestive ulcer, which comprises an effective amount of a polyisoprene compound of the formula

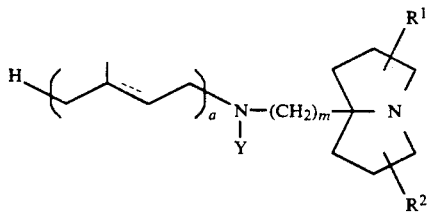

wherein Y is a hydrogen atom or a group of

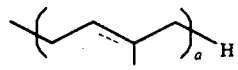

a is an integer of 2–10, $R^1$ and $R^2$ are the same or different and each means a hydrogen atom or an alkyl group having $C_{1-4}$, and m is an integer of 1 or 2, or a salt thereof, in association with a pharmaceutically acceptable carrier or excipient.

6. A pharmaceutical composition as claimed in claim 5, wherein said compound is selected from the group consisting of a) 5-{[(3,7,11,15-tetramethyl-2,6,10,14-hexadecatetraen-1-yl)amino]methyl}-1-azabicyclo[3.3.0]octane;

b) 5-{[(3,7,11,15,19,23,27,31,35,39-decamethyl-2,6,10,14,18,22,26,30,34,38-tetracontadecaen-1-yl)amino]methyl}-1-azabicyclo[3.3.0]octane; and c) 5-{[bis(3,7,11,15-tetramethyl-2,6,10,14-hexadecatetraen-1-yl)amino]methyl}-1-azabicyclo[3.3.0]octane.

7. A pharmaceutical composition for curing a digestive ulcer, which comprises an effective amount of a polyisoprene compound of the formula

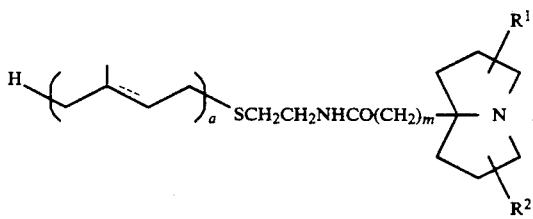

wherein a is an integer of 2–10, $R^1$ and $R^2$ are the same or different and each means a hydrogen atom or an alkyl group having $C_{1-4}$, and m is an integer of 0 or 1, or a salt thereof, in association with a pharmaceutically acceptable carrier or excipient.

8. A pharmaceutical composition as claimed in claim 7, wherein said compound is selected from the group consisting of a) N-[2-(3,7,11,15-tetramethyl-2,6,10,14-hexadecatetraen-1-ylthio)ethyl]-(1-azabicyclo[3.3.0]octan-5-yl)acetamide; and b) N-[2-(3,7,11,15,19,23,27,31,35,39-decamethyl-2,6,10,14,18,22,26,30,34,38-tetraconta-decaen-1-ylthio)ethyl]-(1-azabicyclo[3.3.0]octan-5-yl)acetamide.

* * * * *